United States Patent [19]

Laborit

[11] 4,049,795

[45] Sept. 20, 1977

[54] TREATMENT OF HEMORRHAGIC SHOCK

[75] Inventor: Henri Laborit, Paris, France

[73] Assignee: Centre d'Etudes Experimentales et Cliniques de Physio Biologie de Pharmacologie et d'Eutonologie, Paris, France

[21] Appl. No.: 469,315

[22] Filed: May 13, 1974

Related U.S. Application Data

[63] Continuation-in-part of Ser. No. 143,568, May 14, 1971, abandoned, which is a continuation-in-part of Ser. No. 19,532, March 18, 1970, abandoned, which is a continuation of Ser. No. 670,186, Sept. 25, 1967, abandoned.

[51] Int. Cl.$^2$ .................... A61K 31/70; A61K 31/12
[52] U.S. Cl. ..................................... 424/180; 424/331
[58] Field of Search ............................. 424/180, 331

[56] References Cited

U.S. PATENT DOCUMENTS 3,795,581  3/1974  Deindoerfer et al. ............... 424/331

FOREIGN PATENT DOCUMENTS 1,857M  6/1963  France .................................. 424/331
5,812M  3/1968  France

OTHER PUBLICATIONS

Dispensatory of the United States of America, 25th ed., published by J. B. Lippincott Co., Phila., 1955, pp. 429–433.
Chem. Abst. (1), vol. 70, entry 46146a, 1969.
Chem. Abst. (2), vol. 78, entry 79747r, 1973.
Laborit et al., Revue Agressologie, vol. 6, pp. 743–758, 1965.
Laborit et al., Agressologie, vol. 7, pp. 581–595, 1966.

Primary Examiner—Sam Rosen

[57] ABSTRACT

A method for the reversal of shock including hemorrhagic shock and elevation of blood pressure in warm blooded animals including man. An injectable solution of from about 20 to 100 mg 1 kilogram of body weight per day of dihydroxy acetone in a glucose-water solution is administered to the patient. The therapeutic composition is in a dosage unit of from 200 to 1600mg/100 cc of dihydroxy acetone in a hypertonic 5 to 20% glucose solution in water.

9 Claims, 11 Drawing Figures

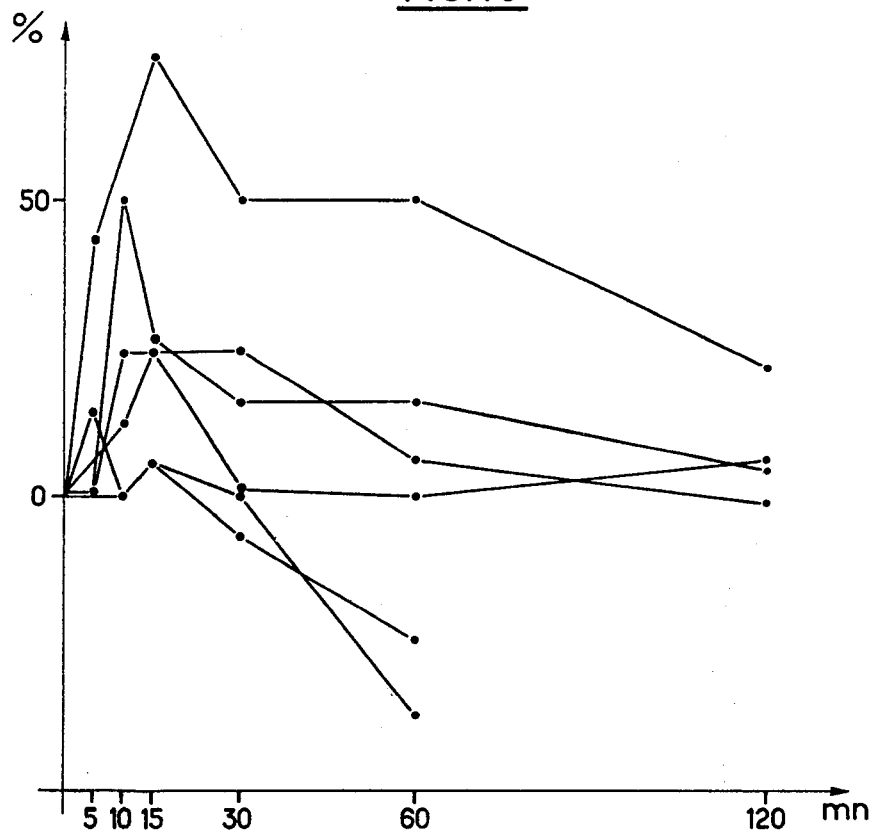
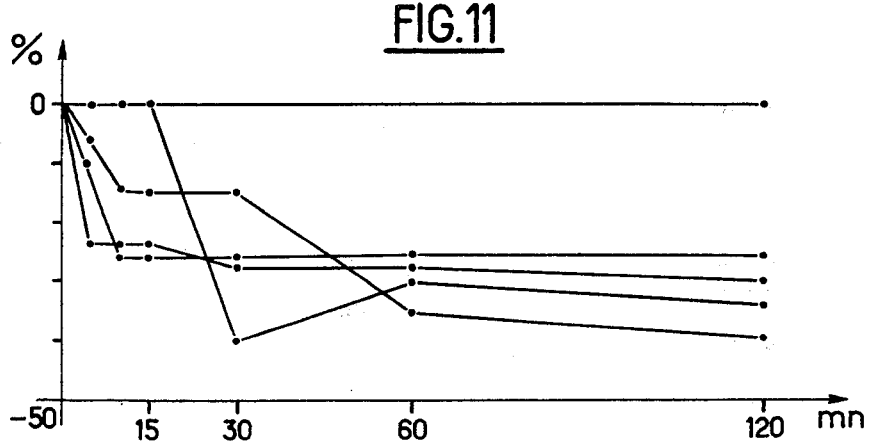

TREATMENT OF HEMORRHAGIC SHOCK

This application is a continuation-in-part of Ser. No. 143,568; filed 5-14-71 which was a continuation in part of Ser. No. 19,532, filed 3-18-70 which was continuation of Ser. No. 670,186, filed 9-25-67, all now abandoned.

BACKGROUND OF THE INVENTION

The present invention relates to the process of treating warm blooded animals including humans who are in an anoxemic state. Specifically it relates to the treatment of lactic acidosis in warm blooded animals and certain conditions of the body believed to be caused by lactic acidosis one of which is hemorrhagic shock.

Lactic acidosis is the clinical term used in medicine to indicate an excessive amount of lactic acid in the blood and other tissues of the organism causing an acidemia. This condition of the tissues manifests itself in patients in various kinds of shock such as hemorrhagic shock, bacteremic shock, postoperative shock of neurogenic origin, myocardial infarction associated with shock, cerebral edema and sequelae of cerebral anoxia.

In 1965 there was published by the applicant a report on the action of dihydroxyacetone in reducing cerebral edema (LABORIT et al Agressologie, Vol. 6, Vol. 6 pp. 743-758, 1965). In this report it was observed that dihydroxyacetone which is a known oxidizing agent for the $NADH_2$ will protect a rat against cerebral lactate edema whether this edema is induced by mechanical means, biological means or pharmacological means.

By mechanical means of generating cerebral edema we refer to extra dural foreign bodies inserted into the brain tissue to cause generation of fluid. By biological means we refer to the generation of cerebral edema by means of a deliberate prefusion of a lactate salt such as sodium lactate which generates lactic acid edema. Finally, by pharmacological means of generating cerebral edema we refer to administration of adrenalin or nicotine to the animal to generate and create a condition of hyperlactacidemia in the test animal.

As a result of that early work, the attention of the applicant was directed to other uses of dihydroxyacetone especially as it effects the phagocytic activity of the organism and its relationship if any to the problems of hemorrhagic shock and the many problems associated with the failures of the vascular system under conditions of shock.

Although mamy treatments of physical or therapeutic nature have been proposed for some of these conditions of shock no satisfactory solution has heretofore been found. For instance of all patients suffering from a heart attack associated with shock, statistics show that 85% will die in spite of prompt attention by physicians.

There is therefore an urgent need for a method and pharmaceutical composition which can treat at least one of these forms of shock. It is an object of the present invention to provide a process for treating the shock induced in warm blooded animals suffering from lactic acidosis. It is also an object of the present invention to disclose and thus provide a pharmaceutical composition in injectable dosage unit form which when administered to animals including humans will reverse the shock symptoms caused by lactic acidosis. It is a specific object of the invention to reverse the depression in blood pressure caused by hemorrhagic shock induced by lactic acidosis and restore that pressure to normal ranges.

BRIEF DESCRIPTION OF THE INVENTION

Accordingly the present invention comprises a method of treating warm blooded animals including humans with an injectable composition in pharmaceutically acceptable liquid dosage form which contains preferably between 30 and 60 milligrams per kilogram of body weight of dihydroxy acetone in a non toxic diluent. The composition is administered intravenously to reverse hemorrhagic shock and elevate the patients blood pressure to normal levels. In the preferred embodiment of the present invention, dihydroxy acetone is administered to said patient by intravenous perfusion in a 10% aqueous glucose solution.

Although we do not intend to be bound by the explanation of exactly how the mechanism of such shock reversal functions we believe the following considerations to be of interest.

A. That immediately following the injection the dihydroxy acetone is transformed into dihydroxy acetone phosphate. The low toxcity of the medication according to the invention therefore results from the fact that dihydroxy acetone phosphate is one of the stages in the conversion of glucose to glycogen in the cell. In fact, dihydroxy acetone phosphate results from the splitting of a fructose-1,6-diphosphate molecule into a glyceraldehyde-3-phosphate molecule and a dihydroxy acetone phosphate molecule. These latter two are balanced and it can thus be seen that the introduction by injection of dihydroxy acetone into the body enables it to act on this balance.

B. It is known also that 3-phospho-glyceraldehyde obtained from fructose-1,6-diphosphate pursues its catabolism to pyruvic acid, and simultaneously this dehydrogenization allows the reduction of two molecules of nicotinamide-adeninedinucletoide, hereafter referred to as NAD, to its reduced form, hereafter referred to as $NADH_2$.

C. It has been found that the reoxidation of the $NADH_2$ coenzyme can be obtained by means of the introduction of dihydroxy acetone compound which is immediately transformed by the organism into dihydroxy acetone-phosphate. In fact, the dihydroxy acetone phosphate is transformed in the cell into α-glycerophosphate and due to the balance previously referred to, this transformation causes a new molecule of glyceraldehyde-3-phosphate to enter into the cycle. Said transformation of the dihydroxy acetone-phosphate is effected at the same time as the oxidation of the $NADH_2$ coenzyme to NAD so that the blockage due to the hyperlactacidemia disappears.

D. It has also been found that the use of the medication administered according to the invention causes the appearance of α-glycerophosphate in the cycle as a result of the dihydroxy acetone-phosphate transformation. This appearance itself has several important meanings. It is an fact known that this compound may be used in mitochondria and its oxidation enables the electron transporting chain to be supplied. It then restores a molecule of dihydroxyacetone-phosphate capable of oxidizing another molecule of extra mitochonidrial $NADH_2$. Thus, the hydrogen resulting from the reduced $NADH_2$ coenzyme situated outside the mitochondria is used inside the said mitochondria. Furthermore, the α-glycerophosphate can also esterify free fatty acids particularly those which are liberated in abundance during attacks under the action of catecholamines. Finally, according to some scientific interpretations, the α-glycerophosphate through the phosphotidic acid which it produced play an important part in the transmembranes carrying of sodium ions enabling them to be expelled outside the cell. All these above scientific findings thus explain the processes by which an injection of dihydroxy acetone acts on an anoxemic state of the certain tissues by for example reaminating glycolysis and forming adenoisine-triphosphate. The resultant advantage flow therefrom.

Dihydroxy acetone acts continuosly on the blood pressure of the patient which after injection recovers and becomes normal as is shown in the examples and tests set out hereinbelow. This is because dihydroxy acetone slowly but more or less continuously decreases the oxygen consumption of the whole system. It acts as a weak but doubtless sufficiently specific oxidizing agent for the $NADH_2$ coenzyme.

In respect to blood pressure elevation or restoration dihydroxy acetone appears to be more active than hypertonic glucose. It for example acts with smaller doses and above all at a time of irreversible shock where hypertonic glucose has no effect.

Hemorrhagic shock is a form of circulatory failure resulting from loss of fluid from a vascular compartment. The fluid loss may occur by hemorrhage or through an increase in capillary permeability. In persons who have been severely burned, have suffered sever traumatic injury or have undergone major surgery the capillaries appear to become permeable to plasma protein and large volume of fluid containing albumin enter the extravascular space thereby reducing the blood volume. The resultant circulatory difficulty leads to impaired blood and oxygen supply to the tissues leading to further capillary injury. Restoration of the circulatory blood volume in shock is of primary importance with the objection of restoring normal volume and blood pressure.

In this regard the use of dihydroxyacetone acts to restore normal blood pressure during such conditions of shock.

Dihydroxyacetone may possibly reanimate phagocyte activity which considerably widens its therapeutic uses. It is particularly useful for reanimation in the treatment of acute anoxemia for example in the treatment of cardiovascular collapse and in particular in the treatment of infarction of the myocardium, in the treatment of intravascular aggregation in protection against accidents due to intra-arterial injection of contrast substances used in radiology. It is useful in the treatment of metabolic acidosis in general, lactic acidosis in particular due to fatigue. It is useful in reactivation treatment of the reticuloendothelium system during infections and allergic states by activation of phagocytosis.

The following examples set forth the several aspects of the present invention. The Example 1 proves the freedom from torcicity of dihydroxyacetone by the lower animal studies.

Example 2 gives the data which explains the conclusion made above that dihydroxyacetone reduces oxygen consumption in the organism (in TABLE I see rat data which shows a mean decrease of 6.5 at a dose level of 2 g / kilogram and 4.1 at a dose level of 4 g / kilogram).

Example 3 reports data on tonus effect of the dihydroxyacetone on the rabbit ileum and the heart muscles of the rabbit.

Example 4 shows that lower animal work on rabbits and dogs indicate that dihydroxyacetone greatly increases hepatic and renal blood flow when intravenously administered. This finding is confirmed by later clinical examples 12 through 16.

Example 5 describes intravenous injection of dihydroxyacetone into a rabbit who had been first perfused with sodium lactate. The induced lactacedemia was reduced by the dihydroxyacetone.

Example 6 merely shows that an intravenous perfusion of dihydroxyacetone causes no change in the EEG and EKG of the test animals.

Example 7 takes up the lower animal studies made with regard to the action of dihydroxyacetone in reversing the blood pressure drop in dogs who were given too successive massive hemorrhages to induce hemorrhagic shock. Intravenous perfusion of from 4 to 7 g / kg of dihydroxyacetone actually elevated the blood pressure an average of 21.5 m of Hg even after fatal hemorrhages were under way in the test animals.

Example 8. This example reports further rabbit studies on induced cerebral anoxemia by (1) clamping (2) hypercapmic anoxemia and (3) nitrogen induced anoxemia. Again in the case of nitrogen induced anoxemia the blood pressure was restored despite the fatally induced anoxemia.

Example 9 relates to the action of dihydroxyacetone in counteracting the depressive effects of lactic acid on the phagocytic activity of the reticulo endothelium system by recognized techniques employed on rabbits in the laboratory. This example cites therefore one more physiological action of dihydroxyacetone.

Example 10 discloses additional work on the action of dihydroxyacetone on the concentration of free fatty acids in blood plasma. The rabbit data was obtained by means of recognized test procedures. The shock action of increased adrenalin causes the level of non esterified acids to rise sharply but the administration of dihydroxyacetone returned the level of these fatty acids to normal.

Example 11 discloses more effects of hemorrhagic shock and how the same is counteracted by the dihydroxyacetone administered in Example 10. In this case the shock result is blood sludging or intravascular aggregation of blood components such as lipids and blood sterols.

Example 12 through 16 give clinical proof of the ability of dihydroxyacetone when injected into several patients suffering from hemmorhagic shock to reverse the depression in blood pressure. The body weights of these patients range from 38 kilos to about 72 kilos and the dosage of dihydroxyacetone from 1 to 25 grams or 1,000 to 25,000 milligrams daily. In the clinical example 12 the shock treated was caused by a brain operation causing sharp depression of blood pressure which was corrected by injection of dihydroxyacetone in aqueous glucose.

In Example 13, 14, 15 and 16 similar cases are reported where the hemorrhagic shock which was successfully reversed arose out of surgery and blood loss or other complications.

In general the effective dosage range in its broad aspects based on these successful clinical applications appears to be from about 1,000 to 25,000 mg of dihydroxyacetone daily when administered from a stock solution of 1 to 8 grams/500 cc of a hypertonic 5 to 20% glucose in water solution. This would work out to about 200 to 1600 mg of dihydroxyacetone per 100 cc of stock solution although the preferred dose range is 30 to 60 mg/kilo as noted above, and top dose 100mg/cc.

The following examples are only set forth to illustrate the invention and the scope thereof can only be measured by the several appended claims. In all instances, dihydroxyacetone was used as a solution in 10% aqueous glucose.

EXAMPLE 1: TOXICITY

Toxicity of dihydroxyacetone was determined by standard procedures. The $LD_{50}$ for intraperitoneal injection in rats was found to be about 8.75 g/kg; the lethal dose is about 9 g/kg The maximum non-lethal dose is about 7.50 g/kg. When toxic doses were administered, tremor and clonic spasms were noted.

In an additional test, five rats each were daily injected intraperitoneally with 7 g/kg. None of the animals died and this dose was completely detoxified within 24 hours following the treatment.

In a further test, 4.5 g/kg of dihydroxyacetone was injected repeatedly to 3 groups of 5 rats each. The first group received this dose (½ of $LD_{100}$) every 4 hours, the second group every 3 hours with no deaths occurring among the 10 test animals. In the third group which received the same dose every 2 hours, 3 animals died. This indicates that half of the lethal dose is completely metabolized in three hours by rats.

It was also established that the maximum non-lethal dose administered orally is about 60 g/kg; of six rats receivingan oral dose of 80 g/kg each, one animal died.

Rabbits tolerate a single dose of 8 g/kg by the intraperitoneal route.

EXAMPLE 2: OXYGEN CONSUMPTION

This series of measurements is intended to confirm the fact that dihydroxyacetone, in accordance with the theory explained above, should considerably reduce the oxygen consumption.

The experiments were carried out using the metabolism apparatus for small animals described by BARGETON and KRUMMHELLER in 1949: each aninal acts as a control for itself and at the time of the control receives an intraperitoneal injection of isotonic saline solution of the same volume as that which it will receive of the test dihydroxyacetone solution. The animals used for this type of test weighed between 230 and 300 g. The results obtained are given as percentage of the control tests in the following table I.

| | Difference between the control measurement and the measurement after injection of dihydroxyacetone | |
|---|---|---|
| Test No. | Injection of 2 g/kg DIHYDROXYACE-TONE | Injection of 4 g/kg DIHYDROXYACETONE |
| 1 | − 5 | − 7 |
| 2 | 0 | + 4 |
| 3 | −18 | −13 |
| 4 | − 2 | − 4 |
| 5 | −16 | − 3.5 |
| 6 | + 1 | + 4 |
| 7 | − 8 | −10 |
| 8 | − 4.5 | − 3 |
| 9 | −13 | MEAN = − 4.1 |
| 10 | − 2 | |
| 11 | −11 | |
| 12 | + 1 | |
| | MEAN = − 6.5 | |

It can easily be seen that injection of dihydroxyacetone decreased the oxygen consumption of the rat.

EXAMPLE 3: EFFECT OF ISOLATED ORGANS a. Rabbit ileum:

Fragments of the ileum were suspended in a 75 ml isolated organ tank containing Tyrode's solution maintained at 37° C by a thermostat and oxygenated by bubbling pure oxygen at a constant rate of flow. The movement of the organ were recorded by means of a lever on a cylinder rotating at a known constant speed.

It was noted that the addition of 50 mg of dihydroxyacetone to 75 ml of survival medium caused only a slight and transient tonus increase. Doses of 400 mg must be reached in order to obtain a clear increase. At a dose of 18, a momentary hypertonia was observed.

Hypertonia caused by adrenalin was clearly decreased by dihydroxyacetone, whereas hypertonia due to acetylcholine did not change. The action of nicotine clearly diminished in the presence of dihydroxyacetone. The hypertonic activity of reducing agents such as vitamin C or amino-ethyl isothiouronium disappeared in the presence of dihydroxyacetone. The same observation was made with serotonin, the hypertonic activity of which seemed to be associated with a reducing power.

Potassium chloride, which ordinarly increases the tonus of the fiber in a stable manner, decreases only the contractile amplitude without affecting the tonus in the presence of dihydroxyacetone. On the other hand, the hypertonic action of sodium lactate on the ileal fiber seems to be influenced to only a small degree by dihydroxyacetone.

b. Rabbit atrium:

The technique used for this study was the same as that described above for the ileum of the rabbit, but replacing the ileum with bled rabbit atrium. The preservation liquid used as LOCKE's liquid.

At a dose of 800 mg per 75 ml of preservation liquid, dihydroxyacetone caused a slight increase in amplitude. When 600 mg of sodium lactate was added subsequently, there was a slight opposition to its inhibitory action. Dihydroxyacetone had no action on the lactate when it was added first. The antagonism is a function of the dose and of limited duration. Dihydroxyacetone has a negative chronotropic action, whereas lactate accelerates the rhythm.

It does not act on the tonus of an isolated segment of aorta.

EXAMPLE 4:

ACTION OF DIHYDROXYACETONE ON HEPATIC AND RENAL CIRCULATION

These experiments were carried out on rabbits and dogs in accordance with the technique developed by LETERRIER and BARON (Agressologie, Vol. 4, No. 2, p. 165 ff of 1963).

It has been noted that an intravenous perfusion of 2 g/kg of dihydroxyacetone caused no pressure disturbance. A slight increase in the average pressure and a widening of the pulse pressure was always noted. In the dog, the response to adrenalin, noradrenalin and serotonin remained unchanged in the presence of dihydroxyacetone.

A solution of dihydroxyacetone in distilled water has a pH of 4 and must therefore be adjusted to bring the pH back to neutrality; without this, a slight fall in the blood pH was noted, whereas the $CO_2$ pressure reamined stable.

In rapid perfusion at a dose of 1 g/kg, dihydroxyacetone variably increased the hepatic and renal flows; the hepatic flow seemed particularly improved, and nearly doubled. The attached drawings demonstrate this graphically.

EXAMPLE 5

Figure 1:
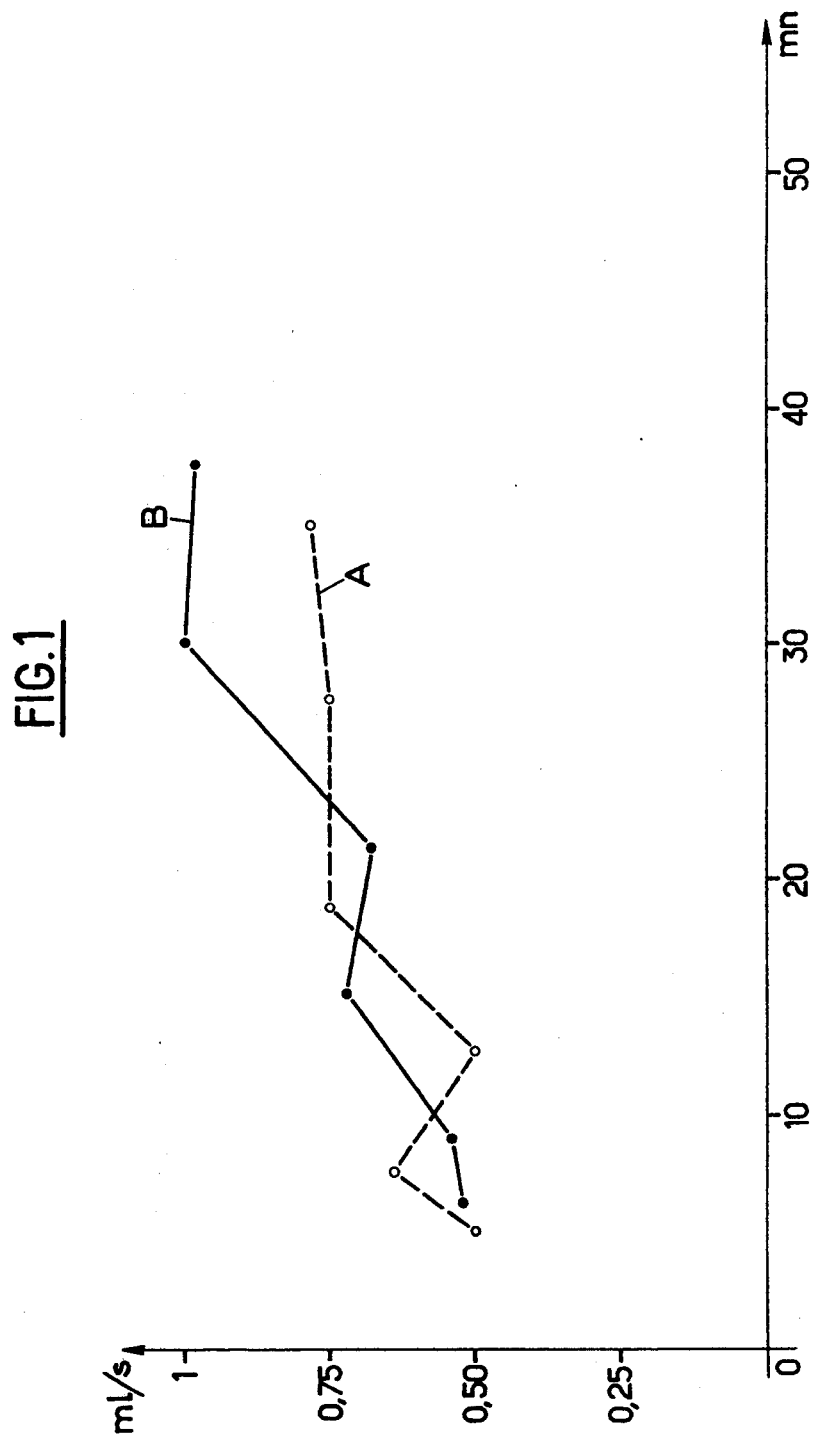
FIG. 1 shows, in ml per second, the variation in the renal flow (curve A) and the variation in the hepatic flow (curve B) as a function of time (in minutes) after an injection of dihydroxyacetone (1 g/kg) at zero time.
Figure 2:
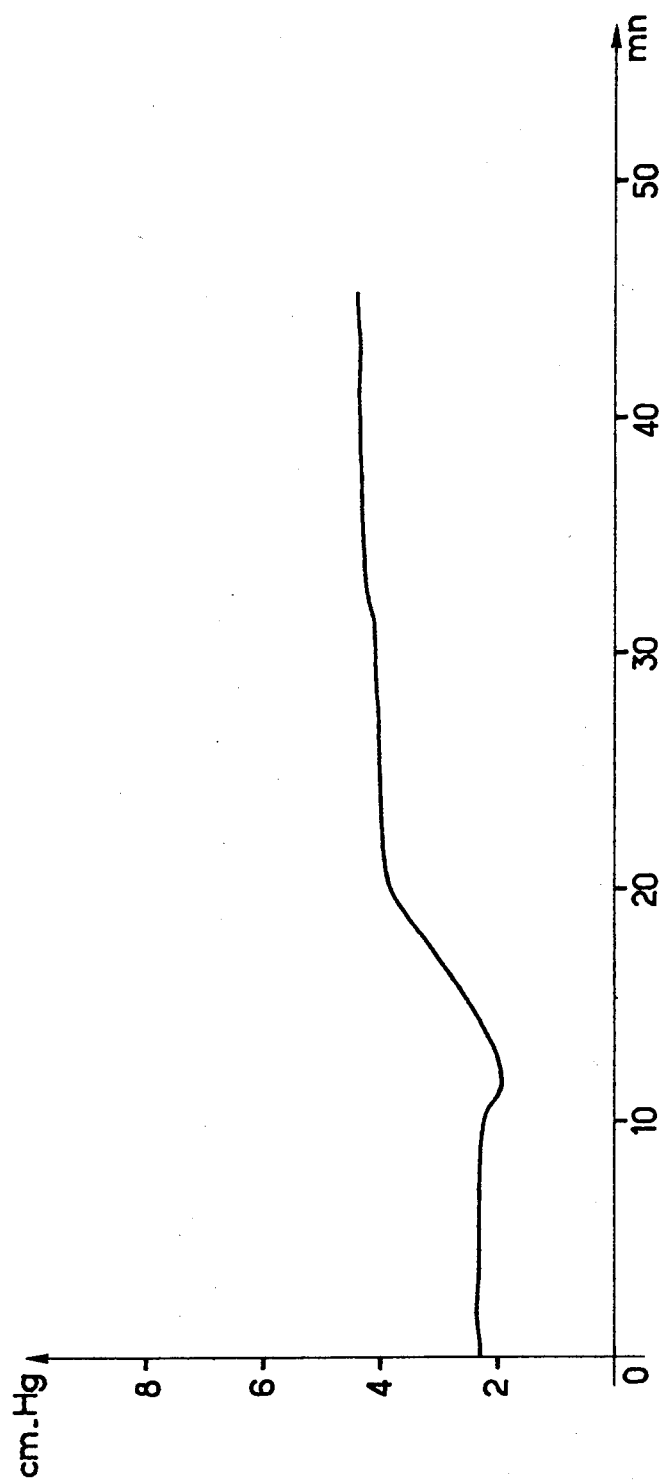
FIG. 2 shows the variation in blood pressure (in cm of mercury) as a function of time (in minutes). The first injection of dihydroxyacetone (1 g/kg) was given 20 minutes after beginning of the measurement, the second injection 4 minutes later, each injection required one minute for completion.

DEVELOPMENT OF GLUCIDIC METABOLISM UNDER INTRAVENOUS PERFUSIONS OF DIHYDROXYACETONE

These tests were carried out on rabbits weighing an average of 2.500 kg.

A trachetomy was carried out under local anaesthesia with procaine. The animal was intubated, and then curarized (intravenous injection of 200 mg of gallamine triethyl iodide) and placed under controlled ventilation by means of an artificial respirator, the frequency and amplitude of which had been regulated to values previously measured in the intact animal, in accordance with the method indicated by WEBER and BARON (Agressologie, Vol. 7, No. 3, p. 279 ff of 1966). A saphenous vein and the two femoral arteries were catheterized under local anaesthesia in order to register the blood pressure by a manometer and to take blood samples; a jugular vein was cathesterized to the base of the skull to sample cerebral venous blood.

The solutions were injected at a constant speed with the apparatus permitting constant speed of infusion at a dose of 66 mg/kg over a period of 15 minutes. The results obtained were compared with those obtained following a perfusion carried out in the same way with sodium d,l-lactate at a dose of 40 mg/kg/min.

The lactacidemia was measured by the enzymatic method described by PFLEIDERER and DOSE (Bicohem. Z., Vol. 326, p. 436 ff of 1955). The glycemia was measured by the enzymatic method in the arterial and cerebral venus blood. The samples were taken before the perfusion, at the end of the perfusion, and at 30 minutes and 60 minutes after perfusion. Lactacidemia reached values lower than those obtained after a perfusion of sodium lactate, but on the other hand, it continued to increase at 30 and 60 minutes after the end of perfusion, whereas in the case of the sodium lactate it tended to return to its initial values. When the perfusion of sodium lactate was followed by a prefusion of dihydroxyacetone, a progressive fall in the lactacidemia was observed, as was the case with sodium lactate alone.

It was also observed that pyrucicemia increased in parallel with lactacidemia and, in some cases, even more than with lactacidemia, so that the ratio between the amounts of lactate to pyruvate decreased in the serum. After a perfusion of dihydroxy acetone, glycemia increased considerably; in fact more than after a perfusion of lactate or pyruvate.

EXAMPLE 6:

ACTION OF DIHYDROXYACETONE ON ELECTROENCEPHALOGRAMS AND ELECTROCARDIOGRAMS OF TREATED ANIMALS

A perfusion maintained at a dose of 2 g/kg of dihydroxyacetone causes no change in the electro-enceophalograms of a dog or a rabbit; particularly, this perfusion dies not seem to favour the formation of slow waves, as is the case with solutions of hypertonic glucose.

Similarly, a perfusion of dihydroxyacetone causes no change in the electro-cardiograms within standard deviations.

EXAMPLE 7:

ACTION OF DIHYDROXYACETONE ON HEMMORHAGIC SHOCKS

These experiments were carried out with dogs. Irreversible shock was obtained by the method of WIGGERS (the Physiology of Shock, Commonwealth Fund, New York 1950), by introducing two successive hemmorhages. Spontaneous reinjection, by progressive circulatory failure, of a quarter of the mass of blood effused during the second hemmorhage, was chosen as the irreversibility criterion. The following parameters were measured: pH, arterial and venous $CO_2$ pressure (with a radiometertype apparatus), lactacidemia, pyruvicemia and glycemia (by the enzymatic method), and kalemia (with a flame photometer). Samples were taken from the dogs before irreversibility, immediately after, one hour 1½ hours and 2R hours thereafter. The blood pressure was followed by femoral intubation and recorded with an apparatus providing mean arterial bloodpressure readings.

The treated animals received doses of dihydroxyacetene varying from 4 to 7 g/kg of perfusions extending over a period of about 3 hours and the following changes were observed. Glycomia rose above its initial level, kalemia rose above that of the control animals, lactacidemia reached values higher than in the control animals, but pyruvicemia continued to rise, whereas in the control animals it fell. This shows that the excess lactate diminished more quickly in the animals treated with dihydroxyacetone than in the control animals, and that the inhibition of glycolysis, which seems to accompany irreversible shock, does not appear after the injection of dihydroxacetone. The arterial and venous $CO_2$ pressures and the pH developed in a similar manner to those existing in the control animals.

The measurement showing the strongest influence by dihydroxyacetone in hemorrhagic shock was blood pressure. The difference between the values of the blood pressure at the end of the reinjection of effused blood and after the perfusion of dihydroxyacetone were always positive and the average of these differences was 21.5 mm Hg. This rise in the blood pressure was stable and was maintained for several hours; the development of irreversible hemorrhagic shock as thus prolonged, death being delayed about 2 to 4½ hours. Particularly noteworthy was the finding tht the injection of dihydroxyacetone had a favorable effect on the blood pressure, whereas 30% glucose had none.

EXAMPLE 8:

ACTION OF DIHYDROXYACETONE ON CEREBAL ANOXEMIA

The tests were done on rabbits weighing an average of 2.5 kg. The fastening of the cranial electrodes was done under local anaesthersia with procaine, as was the placing of the catheters in a femoral artery to record the blood pressure. The tracheotomies and tracheal intubations were also done under local anaesthesia using procaine. The temperature was maintained at around 38° C. Three types of anoxemia were investigated;

1. Elective cerebral anoxemia by stopping cerebral circulation (anoxemia by clamping): Artificial ventilation was set up by an apparatus allowing constant volume and speed of respiration. An upper sternatomy of the manubrium was carried out; the left sub-clavian artery, the left carotid artery and the right trucus brachiocephalicus were isolated. The clamps were then put into place according to the technique described by NIAUSSAT and LABORIT (Conference of d Agressologie Cycle, Vol. 1, p. 15 ff of 1959). The artifically ventilated animal preserved good peripheral cardiovascular dynamics during the ischemia and supported 120 seconds of clamping without severe hypotension.
2. Hypercapnic anoxemia: The above-mentioned artificial ventilation of the animal after curarization was stopped. Stopping of the cerebral electrogenesis was obtained after an average of 120 seconds.
3. Nitrogen anoxemia: The animal was curarized and artifically ventilated as indicated above. Anoxemia was obtained by connecting a nitrogen gasbag to the air intake of the BEAUDOUIN apparatus; general non-hypercapnic anoxemia occurred. Air was replaced after 120 seconds. Dihydroxyacetone was administered intravenously with an apparatus permitting constant speed of infusion at a dose of 1 g/kg injected within a period of 15 minutes. A latency of 30 minutes was observed before anoxemia was caused.

With prior prefusion of dihydroxyacetone, survival time was slightly increased during the first of the three abovementioned types of anoxemia. The gain was considered minor in the case of nitrogen anoxemia and anoxemia by clamping, but was pronounced in hypercapnic anoxemia.

In regards to recuperation latency, a perfusion of dihydroxyacetone caused a slight improvement in the case of nitrogen anoxemia, an improvement which was difficult to measure in the case of hypercapnic anoxemia, and there was no improvement at all in the case of anoxemia by clamping.

As regards the recuperation time, there was a clear improvement in the case of hypercapnic anoxemia (not exceeding 30 seconds for 2 minutes of anoxemia) but no improvement in the two other cases.

It was also observed that the blood pressure, which, in the case of nitrogen anoxemia, underwent a sharp fall after rising during the first minute, maintained a high value when anoxemia was preceded by a prefusion of dihydroxyacetone.

EXAMPLE 9:

ACTION OF DIHYDROXYACETONE ON THE PHAGOCYTIC ACTIVITY OF THE RETICULO-ENDOTHELIAL SYSTEM

The technique described by HALPERN in 1954 was used. That technique is based on the study of the kinetics of the disappearance in the blood of particles of carbon injected into the vein. The kinetics of disappearance follow the equation $$K = \frac{\log C_1 - \log C_2}{T_2 - T_1}$$

in which formula $C_1$ is the concentration of carbon in the blood at time $T_1$ and $C_2$ is the concentration of carbon in the blood at time $T_2$, K being a constant. The constant K, called phagocytic index, represents the phagocytic activity of the cells of the reticule-endothelial system under the experimental conditions. For the tests, the technique and carbon suspension described by STIPPEL (J. Physiol. of Paris, Vol. 50, p. 911 ff of 1958) were used. The study was done on rabbits of the same stock, male or female, or an average weight of about 2.5 kg, devided into four batches of four animals each.

The first batch was used as controls and received, by slow intravenous injection, 10 ml of a 0.8% solution of sodium chloride ten minutes before the injection of 4 mg of carbon per 100 g of animal. The second batch received an injection of 10 ml of a lactic acid solution at a dose of 0.9 g/kg followed within 10 minutes by an injection of 4 mg of carbon per 100 g of animal. The third batch received an injection of 10 ml of a dihydroxyacetone solution at a dose of 1 g/kg followed within ten minutes by an injection of 4 mg of carbon per 100 g of animal. The fourth batch received an injection of 5 ml of a dihydroxyacetone solution at a dose of 1 g/kg followed within ten minutes by an injection of 5 ml of a lactic acid solution at a dose of 0.9 g/kg, and followed after another 10 minutes with an injection of 4 mg of carbon per 100 g of animal.

In all the tests, a total volume of 10 ml was injected with a fairly closely related injection speed (less than five minutes).

Figure 3:
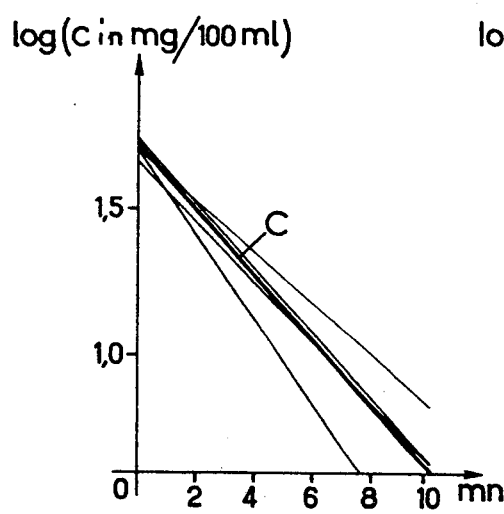
Figure 4:
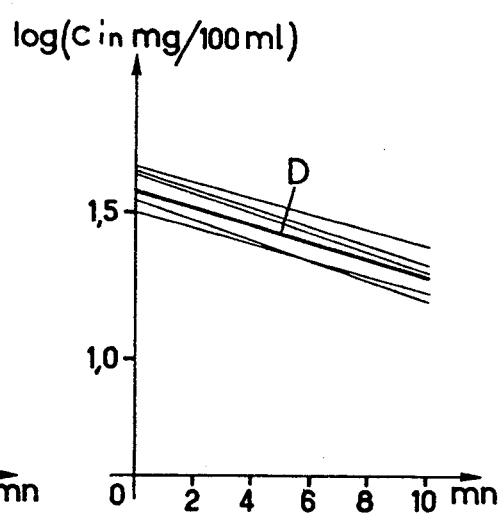
Figure 5:
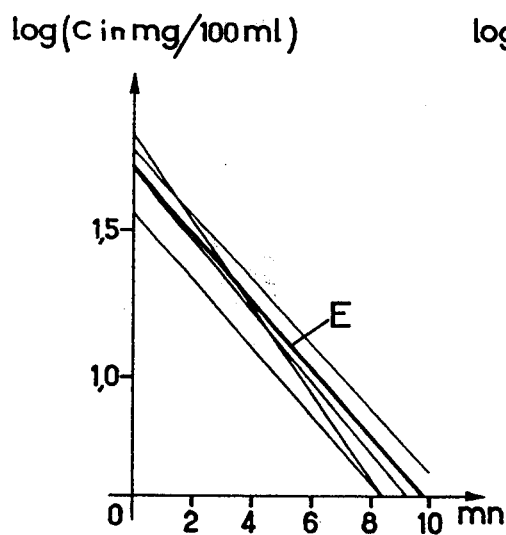
Figure 6:
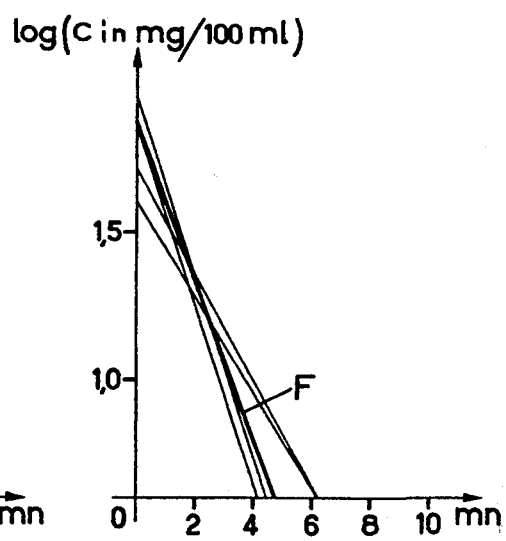
Figure 7:
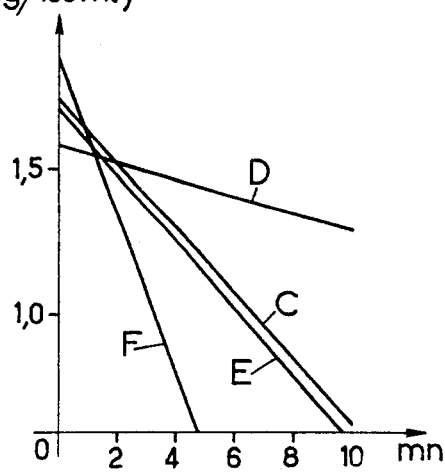

FIG. 3 shows the variation of the logarithm of the concentration of carbon in the blood as a function of the time expressed in minutes for each animal of the first batch subjected to the test described; FIG. 4 shows the curves giving the same variations for the second batch of animals; FIG. 5 shows the curves giving the same variations for the third batch; FIG. 6 shows the curves giving the same variations for the fourth batch. The slope of the lines enables the calculation of the value of the phagocytic index K; FIG. 7 shows the average curves relative to each of the batches.

From these graphs it will be seen that the rate of phagocytosis increased in the animals which were injected with sodium d,l-lactate (FIGS. 3 and 4)/. FIG. 5 shows that injection of dihydroxyacetone creates practically no change in the speed at which the carbon particles disappear with respect to the speed in the control animals. FIG. 6 shows that the injection of dihydroxyacetone carried out 10 minutes before that of lactic acid counteracts the depressive action of the latter on the phagocytic index and considerably increases the speed of purification of the carbon particles with respect to the control animals.

EXAMPLE 10

ACTION OF DIHYDROXYACETONE ON THE VARIATIONS IN THE CONCENTRATIONS OF FREE FATTY ACIDS IN THE PLASMA

Doses of 1 and 2 mg of adrenalin were introduced subcutaneously into rabbits weighing 2.5 to 3.5 kg. Between 5 and 10 minutes after the injection of adrenalin, dihydroxyacetone was administered by the marginal vein of the ear (the injection of dihydroxyacetone was made at zero time when the amimal had been kept without food for only 24 hours). The amount of non-esterified fatty acids in the plasma was determined by the method described by DOLE (J. Clin. Invest., Vol. 35, p. 50 of 1956) and by DOLE and MINERTY (J. Biol. Chem., Vol. 235, p. 2595 of 1960).

Figure 8:
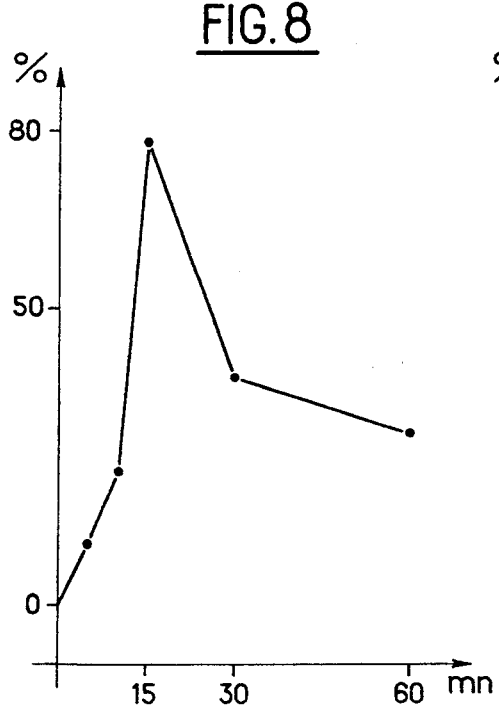
Figure 9:
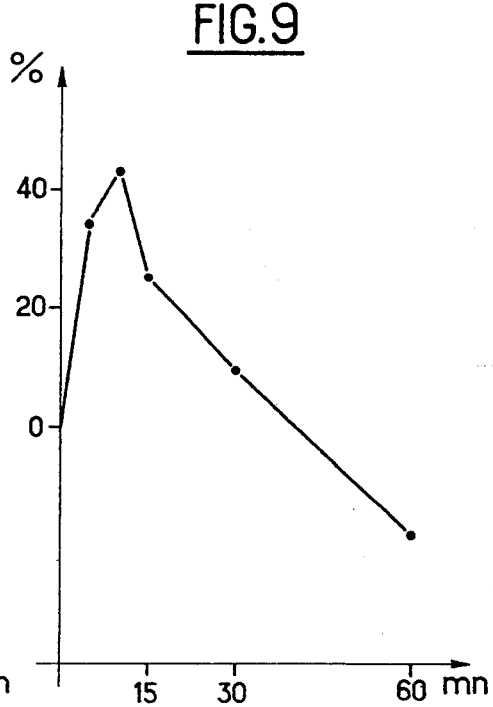

FIGS. 8, 9 and 10 show the variation in the percentage of non-esterified fatty acids in the plasma as a function of the time. The curve of FIG. 8 shows the results obtained by injecting 2 mg of adrenalin at zero time; the curve of FIG. 9 shows the results obtained by injecting 1 mg of adrenalin at zero time. Both curves are averages determined from 3 animals, FIG. 10 shows the recorded variation for animals which underwent at zero time an injection of 1 mg of adrenalin and between time 5 and time 10 (in minutes) underwent an injection of 1 g/kg of dihydroxyacetone. The graphs demonstrate that the average proportion of non-esterified fatty acids increased about 10 to 15 minutes after the injection of adrenalin. At the end of a time lapse of one hour after the injection, these proporations again increased in the case of injection of 2 mg of adrenalin (FIG. 8), but fell below normal in the case of administration of only 1 mg (FIG. 9).

In the case of administration of dihydroxyacetone, (FIG. 10) variable disturbances were noted, but general tendency toward increased percentages of non-esterified fatty acids in the plasma was indicated.

FIGS. 8, 9 and 10 correspond to variations obtained from animals which had been fed. In contrast thereto, FIG. 11 shows the variations obtained from animals which had been kept without food for 24 hours. These animals showed an abnormal increase (About 40%) in the percentage of non-esterified fatty acids: an injection of 1 g/kg of dihydroxyacetone caused the percentage of non-esterified fatty acids in the plasma to return to normal.

EXAMPLE 11:

ACTION OF DIHYDROXYACETONE ON THE ERYTHROCYTIC AGGREGATION OF THE MICROCIRCULATION (SLUDGE)

This phenomenon was observed by using the technique developed by LETERRIER AND BRUE (Agressologie, Vol. 4, No. 3, p. 299 ff of 1963): it entails a microscopic observation of the mesenteric circulation of the rabbit.

The appearance of "sludge" was caused by different known methods: hemorrhagic shock, perfusion of noradrenalin or adrenalin, perfusion of sodium d,l-lactate leading to lactacidemia of 100 mg per 100 ml, and perfusion of ethyl alcohol. The hemorrhagic shock was obtained by the WIGGERS method. The perfusion of adrenalin was carried out at a dose of 10 mg/kg/min. for 10 to 15 minutes. The perfusion of lactate was effected at a dose of 0.39 g/min for 15 minutes. The perfusion of ethyl alcohol (in a 20% aqueous solution) was carried out at a dose of 20 ml of solution (i.e. 4 ml of absolute alcohol) for 15 minutes.

It was observed that independent of the experimental cause of sludge, the dihydroxyacetone caused the intravascular aggregation to disappear and re-established the mesenteric capilliary circulation, even when the vessels were almost completely blocked.

CLINICAL EXAMPLES OF HUMAN USE
CLINICAL EXAMPLE 12:

A 62 year old female who had suffered from high blood pressure for a long time underwent an urgent operation for the removal of an intra-cerebral hematoma. During the night following the operation, the blood pressure varied between 70 and 100 mg Hg in spite of the perfusion of two units (800ml) of isogroup-isorhesus blood and (500ml) of a 30;% glucose solution combined with insulin (one unit per 4 g of glucose) and with 1 g of calcium chloride. Her usual blood pressure was between 180 and 200 mm of mercury.

A first injection of 2 g of dihydroxyacetone caused the pressure to rise from 90 to 130 mm Hg in one hour; after two hours, it fell back to 95 mm Hg. After second injection of 2 g of dihydroxyacetone in the perfusion tube of 10% glucose solution, her blood pressure rose to and subsequent remained at 130 mm Hg without other forms of treatment.

CLINICAL EXAMPLE 13

A normotensive 54 year old male who had a straightened arch of the aorta and an enlarged left ventrical was undergoing surgery for the removal of a temporal tumour. After an hour of the operation, the blood pressure, which at the beginning had been 100 mm Hg, fell to 60 mm Hg and did not rise in spite of a perfusion of two units of blood (800ml) and 500 ml of 30% glucose combined with insulin (one unit per 4 g of glucose), potassium (20 mEq of lactate), and 1 g of calcium chloride.

Two grams of dihydroxyacetone were then injected over a period of 15 minutes: the blood pressure rose to 100 mm Hg and remained there until the end of the operation. There were no post-operative complications.

CLINICAL EXAMPLE 14

A 66 year old male who had suffered from high blood pressure and cardiac arrhythmias, was undergoing an operation for the removal of a bilateral sub-dural hematoma. During the operation, his blood pressure fell to 70 mm Hg. Two grams of dihydroxyacetone were injected: within 20 minutes the blood pressure rose to 130 mm Hg and 45 minutes later recovered its initial value of 170 mm Hg.

CLINICAL EXAMPLE 15

A 73 year old female of generally good health but who had undergone surgery in the previous month for the excision of a cancer of the cecum, was undergoing an operation for a cerebral metastasis. During the operation, a drop in blood pressure to 60 mm Hg occurred, while the normal blood pressure of the subject was about 150 mm Hg. The blood pressure drop could not be reversed in spite of administering one unit of blood. However, a perfusion of 2 g of dihydroxyacetone caused the pressure to rise within 15 minutes to 110 mm Hg which remained constant thereafter. There were no post-operative complications.

CLINICAL EXAMPLE 16

A 74 year old male who did not suffer from high blood pressure and who was in good general state was undergoing an operation for a meningioma of the falx. During the operation a drop in blood pressure to 80 mm Hg occurred. A perfusion of two units of blood (800 ml) was effected to compensate for the moderate blood losses. At first, the pressure rose slowly, but dropped subsequently to 80 mm Hg. An injection of 3 g of dihydroxyacetone was given, which produced an initial rise in blood pressure to 120 mm Hg and then stabilized at 100 mm Hg. There were no post-operative complications.

It will be seen from the above examples that the injection of dihydroxyacetone had a pronounced and beneficial effect on animals and humans suffering from lactic acidosis without undesirable side effects. While dihydroxyacetone can be injected directly as an aqueous solution, the preferred solution contains aside from said dihydroxyacetone about 5 to 20% by weight of glucose or other pharmaceutically acceptable hexoses. The injectable solution of dihydroxyacetone in aqueous glucose may, of course, contain other excipients, particularly a preservative, a stabilizer, a buffer and other components often included as minor quantities in the preparation of injectable solutions. The preferred concentration for dihydroxyacetone is between 0.2–1.6% by weight based on the total weight of the solution. A stock solution thus comprises 1–8 g of dihydroxyacetone in 500 ml of a 5–20% glucose solution. Dosages of 2,000 to 3,000 mg of dihydroxyacetone may be employed as well as 5 to 25 per cent by weight of aqueous glucose solution.

I claim:

1. A method of treating shock in humans to reverse the same and elevate blood pressure which comprises intravenously administering to a patient in need thereof a therapeutically effective amount of a pharmaceutically acceptable injectable solution containing from about 200 to 1600 mg of dihydroxyacetone per 100 cc of a pharmaceutically acceptable hypertonic glucose solutions diluent.

2. A method according to claim 1 wherein the pharmaceutically acceptable diluent is a hypertonic aqueous glucose solution.

3. A method according to claim 1 wherein the pharmaceutically acceptable diluent is a hypertonic solution of 5 to 20% by weight of glucose in water solution.

4. A method according to claim 1 wherein the patient is intravenously injected with from 2000 to 3000 mg. dihydroxyacetone.

5. A method according to claim 4 wherein the dihydroxyacetone is administered as a solution in a hypertonic 5 to 20% by weight glucose in water solution.

6. An injectable pharamceutical solution in liquid dose form suitable for intravenous administration to reverse shock and elevate blood pressure in humans which comprises an injectable dose of 200 to 1600 mg/100 cc of dihydroxyacetone in a pharmaceutically acceptable hypertonic glucose liquid diluent.

7. An injectable solution according to claim 6 wherein the pharmaceutically acceptable liquid diluent is an aqueous hypertonic glucose solution.

8. An injectable solution according to claim 6 wherein the aqueous hypertonic glucose solution contains from 5 to 25 per cent by weight of glucose.

9. An injectable solution according to claim 7 wherein the aqueous hypertonic glucose solution is a 10 percent by weight glucose solution.

* * * * *